United States Patent
Tommasi et al.

(10) Patent No.: US 11,581,069 B2
(45) Date of Patent: *Feb. 14, 2023

(54) INTELLIGENT GENERATION OF CUSTOMIZED QUESTIONNAIRES

(71) Applicant: INTERNATIONAL BUSINESS MACHINES CORPORATION, Armonk, NY (US)

(72) Inventors: Pierpaolo Tommasi, Dublin (IE); Marco Luca Sbodio, Dublin (IE); Vanessa Lopez Garcia, Dublin (IE); Sebastian Michael Lehrig, Dublin (IE); Natalia Mulligan, Dublin (IE)

(73) Assignee: INTERNATIONAL BUSINESS MACHINES CORPORATION, Armonk, NY (US)

( * ) Notice: Subject to any disclaimer, the term of this patent is extended or adjusted under 35 U.S.C. 154(b) by 230 days.

This patent is subject to a terminal disclaimer.

(21) Appl. No.: 16/389,736

(22) Filed: Apr. 19, 2019

(65) Prior Publication Data
US 2020/0335183 A1   Oct. 22, 2020

(51) Int. Cl.
*G16H 10/20*   (2018.01)
*G06N 20/00*   (2019.01)

(52) U.S. Cl.
CPC .......... *G16H 10/20* (2018.01); *G06N 20/00* (2019.01)

(58) Field of Classification Search
CPC ................. G16H 10/20; G06N 20/00
See application file for complete search history.

(56) References Cited

U.S. PATENT DOCUMENTS

| 4,130,881 | A | 12/1978 | Haessler et al. |
| 6,584,445 | B2 | 6/2003 | Papageorge |
| 7,092,821 | B2* | 8/2006 | Mizrahi ............ A63F 13/10 705/500 |
| 2002/0035486 | A1 | 3/2002 | Huyn et al. |
| 2003/0004788 | A1 | 1/2003 | Edmundson et al. |
| 2005/0065813 | A1 | 3/2005 | Mishelevich et al. |
| 2006/0218007 | A1* | 9/2006 | Bjorner ............ G06Q 10/10 434/258 |
| 2008/0065471 | A1* | 3/2008 | Reynolds ........ G06Q 30/0201 705/7.32 |
| 2009/0030945 | A1* | 1/2009 | Miller .............. G06F 16/248 |
| 2011/0276507 | A1* | 11/2011 | O'Malley .......... G06Q 10/00 705/321 |
| 2012/0084101 | A1 | 4/2012 | Qadri |
| 2013/0297265 | A1* | 11/2013 | Baloch ............ A61B 34/10 703/1 |
| 2014/0046682 | A1* | 2/2014 | Soto ................ G16H 50/30 705/2 |

(Continued)

OTHER PUBLICATIONS

V. Lopez, "Note Highlights: Surfacing Relevant Concepts from Unstructured Notes for Health Professionals," 2017 IEEE International Conference on Healthcare Informatics (ICHI), Park City, UT, 2017, pp. 198-207 (10 Pages).

(Continued)

*Primary Examiner* — Jay M. Patel
(74) *Attorney, Agent, or Firm* — Griffiths & Seaton PLLC

(57) ABSTRACT

Embodiments for intelligent generation of customized questions or questionnaires by a processor. One or more customized questions or questionnaires may be generated according to a user profile, similar profiles of alternative users, one or more historical interactions with the alternative users, one or more goals defined by a domain experts, domain knowledge, historical questions or questionnaires, or a combination thereof using a machine learning operation.

17 Claims, 7 Drawing Sheets

(56) References Cited

U.S. PATENT DOCUMENTS

| | | | |
|---|---|---|---|
| 2014/0114680 A1* | 4/2014 | Mills | G16H 50/30 |
| | | | 705/2 |
| 2014/0229199 A1 | 8/2014 | Beckley | |
| 2015/0262498 A1* | 9/2015 | Wicka | G09B 7/02 |
| | | | 434/362 |
| 2015/0302436 A1* | 10/2015 | Reynolds | G06Q 10/06 |
| | | | 705/7.32 |
| 2015/0326625 A1* | 11/2015 | Rosenberg | G06Q 10/101 |
| | | | 715/753 |
| 2016/0004831 A1* | 1/2016 | Carlson | G16H 10/20 |
| | | | 705/2 |
| 2016/0045317 A1* | 2/2016 | Lang | A61F 2/30942 |
| | | | 700/98 |
| 2017/0000422 A1* | 1/2017 | Moturu | A61B 5/0022 |
| 2017/0109226 A1* | 4/2017 | Ash | G06F 12/0815 |
| 2017/0245759 A1* | 8/2017 | Jain | G16H 50/30 |
| 2017/0262604 A1* | 9/2017 | Francois | G16H 10/60 |
| 2017/0262609 A1* | 9/2017 | Perlroth | G16H 10/60 |
| 2017/0308671 A1* | 10/2017 | Bahrami | G16H 10/60 |
| 2018/0189457 A1* | 7/2018 | Plummer | G16H 50/20 |
| 2018/0189691 A1* | 7/2018 | Oehrle | G06N 7/005 |
| 2020/0176129 A1* | 6/2020 | Salwan | H04N 7/147 |

OTHER PUBLICATIONS

X. Kortum, 2017, "A Dynamic Adaptive Questionnaire for Improved Disease Diagnostics." In: Adams N., Tucker A., Weston D. (eds.) Advances in Intelligent Data Analysis XVI. IDA 2017. Lecture Notes in Computer Science, vol. 10584 Springer, Cham. (11 Pages).

* cited by examiner

INTELLIGENT GENERATION OF CUSTOMIZED QUESTIONNAIRES

BACKGROUND OF THE INVENTION

Field of the Invention

The present invention relates in general to computing systems, and more particularly to, various embodiments for intelligent generation of a customized questionnaire by a processor.

Description of the Related Art

In today's society, consumers, business persons, educators, and others use various computing network systems with increasing frequency in a variety of settings. The advent of computers and networking technologies have made possible the increase in the quality of life while enhancing day-to-day activities. For example, many individuals require extensive use of technology relating to the health and the medical field. As great strides and advances in technologies come to fruition, the greater the need to make progress in these systems advantageous for efficiency and safety such as, for example, for using the vast amount of available data to recognize impacts on a health state or health of a person.

SUMMARY OF THE INVENTION

Various embodiments for intelligent generation of customized questions or questionnaires using one or more processors, are provided. In one embodiment, by way of example only, a method for implementing intelligent generation of questions or questionnaires, again by a processor, is provided. One or more customized questions or questionnaires may be generated according to a user profile, similar profiles of alternative users, one or more historical interactions with the alternative users, one or more goals defined by a domain experts, domain knowledge, historical questions or questionnaires, or a combination thereof using a machine learning operation.

BRIEF DESCRIPTION OF THE DRAWINGS

In order that the advantages of the invention will be readily understood, a more particular description of the invention briefly described above will be rendered by reference to specific embodiments that are illustrated in the appended drawings. Understanding that these drawings depict only typical embodiments of the invention and are not therefore to be considered to be limiting of its scope, the invention will be described and explained with additional specificity and detail through the use of the accompanying drawings, in which.

DETAILED DESCRIPTION OF THE DRAWINGS

Figure 1:
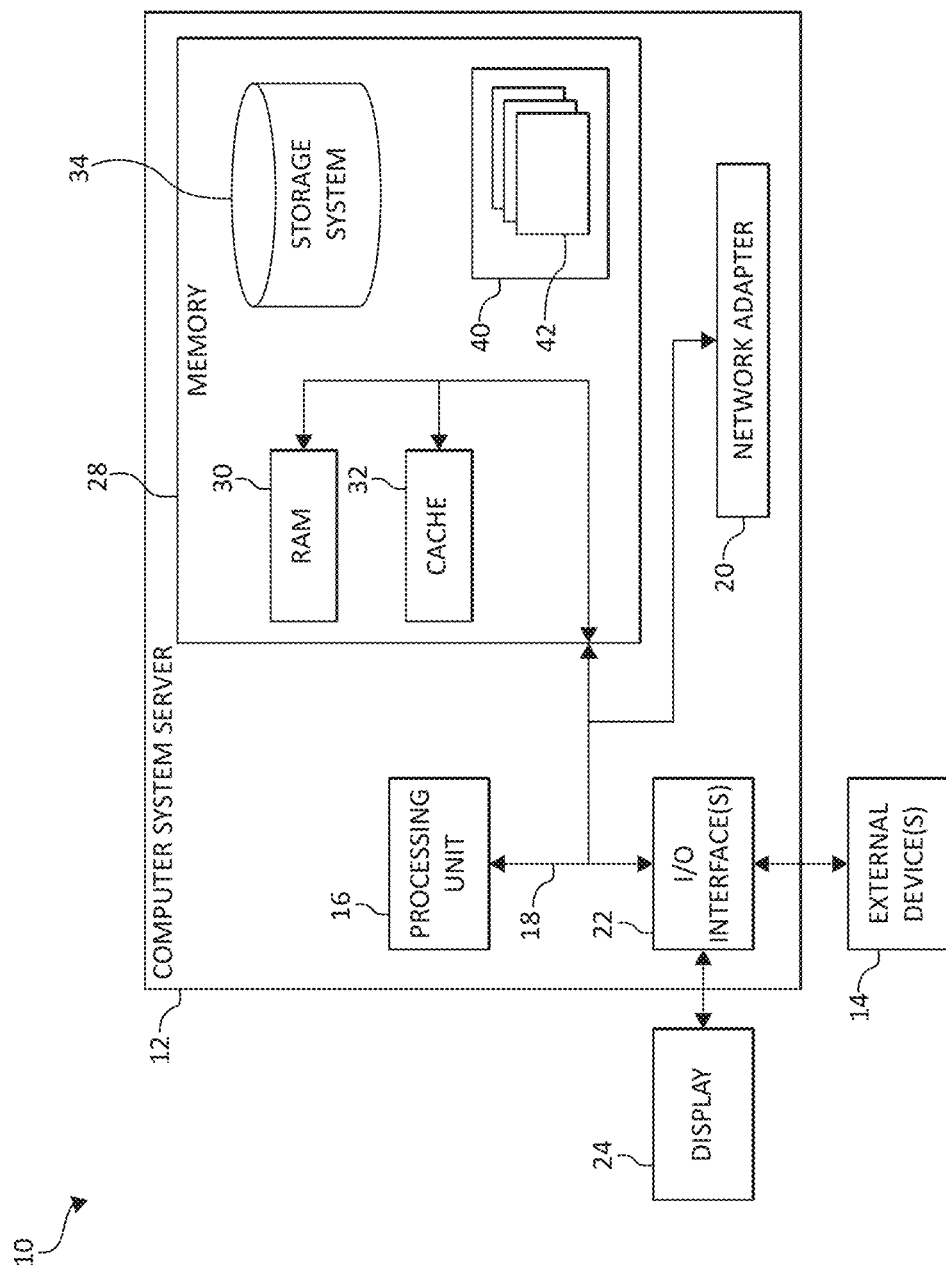
FIG. 1 is a block diagram depicting an exemplary computing node according to an embodiment of the present invention.

Computing systems may include large scale computing called "cloud computing," in which resources may interact and/or be accessed via a communications system, such as a computer network. Resources may be software-rendered simulations and/or emulations of computing devices, storage devices, applications, and/or other computer-related devices and/or services run on one or more computing devices, such as a server. For example, a plurality of servers may communicate and/or share information that may expand and/or contract across servers depending on an amount of processing power, storage space, and/or other computing resources needed to accomplish requested tasks. The word "cloud" alludes to the cloud-shaped appearance of a diagram of interconnectivity between computing devices, computer networks, and/or other computer related devices that interact in such an arrangement.

Moreover, dialog systems can play a key role in the functioning of an entity, such as a business, government, group or other organization. For example, many critical decisions may result from discussions in chat systems, or chat-like conversation systems or chatbots. A chatbot may be an operation which conducts a dialog or conversation, audible, visual, and/or via textual methods. Various entities and/or industries (e.g., the healthcare industry) may seek to capture and analyze these decisions to make various improvements to a structure of the organization. For example, in the medical domain, a need exists for automatically providing a questionnaire to assess a patient's status and to identify their needs (e.g., for identifying an appropriate health program for the patient). Thus, the present invention provides a solution to automatically generate personalized questionnaires to collect user (e.g., client) information.

In one aspect, the present invention provides for intelligent generation of a customized questionnaire and leveraging a dialog system in a computing environment. One or more anomalous records may be identified in a knowledge base. One or more customized queries may be generated for according to a client profile, similar profiles of alternative clients, one or more historical interactions with the alternative clients, one or more goals defined by a domain expert, a domain knowledge, historical queries, or a combination thereof using a machine learning operation.

In an additional aspect, the present invention generates one or more customized/personalized questions and then compiles the customized/personalized questions into one or more questionnaires. One or more of the questionnaires may be executed and/or provided to a client using a dialog system by asking the client one or more of the customized/personalized questions from the compiled questionnaires.

In an additional aspect, mechanisms of the illustrated embodiments may generate customized questionnaires for a selected client (e.g., a patient, business entity, customer, user, employee, etc.) based on a variety of input data. A user may be defined as, for example, a human (e.g., patient), a client and/or customer of a business (either an entity or human), and/or an entity/person that has previously interacted with one or more components of the present invention. The user may be an entity/person interacting with the present invention as described herein. Specifically, a "user of the present invention" may be a "client" who is answering one or more questions/questionnaires generated by the system. A "client" may be a patient in the medical domain, a customer in a marketing domain. A "domain expert" may be an entity/person providing feedback to one or more questions generated by the present invention as described herein. The input data may include a client profile and history, similarity of the client with other (anonymized) client profiles, history of interactions with other (anonymized) clients, goals (formulated as text) defined by one or more domain experts. The generated questionnaires may be automatically executed using a plan-based dialogue system, and/or reviewed and used by a domain expert. For automatic execution, the present invention may dynamically re-generate one or more questions based on the responses/answers to one or more previous questions. In one aspect, the present invention may collect feedback information. The present invention may learn if the questions are relevant for a given context based on the collected feedback. In one aspect, the collected feedback includes both explicit feedback from domain experts, and various forms of implicit feedback. Examples of implicit feedback include, for example, identifying questions skipped by either the client or the domain expert.

To further illustrate, consider the following example. Assume a patient recently diagnosed with diabetes is enrolled into a medical program to manage the health and care of the patient, in terms of medication adherence, mental health and other (chronic) clinical conditions that may be associated to diabetes. Because it is critical to assess the well-being, risk factors and progress of a patient, the present invention may automatically generate one or more customized questionnaires to assist a domain expert (e.g., a care coordinator, nurses, doctors, counselors, etc.) to make critical decisions that are relevant and customized for that particular patient. Moreover, since the available time with a patient is limited, the present invention may generate a set/flow of questions through a set of similarity operations based on the data available for the patient history, the history of other patients (e.g., enroll in the same program or with a similar profile), history of interactions, goals (formulated as text) defined by one or more domain experts, and/or a domain knowledge such as scientific medical literature, guidelines, databases or knowledge graphs.

Assume also in the example that the patient profile indicates a variety of ADLs, behaviors, medical conditions, and/or symptoms. Thus, the present invention may analyze the input data (e.g., client profile, similar profiles of alternative clients, one or more historical interactions with the alternative clients, one or more goals defined by a domain expert, a domain knowledge, historical queries, or a combination) and may identify evidence of occasional drinking from previous medial file/case notes. Based on similarity metrics by comparing the current client with other clients, alternative client may be identified as "similar" according to the input data that indicates the alternative clients experience similar ADLs, behaviors, medical conditions, and/or symptoms. The present invention may prioritize and generates candidate questions to assess, for example, a health/wellness status of the client according the type of symptoms, conditions, and/or responses (e.g., the ADLs, behaviors, medical conditions, and/or symptoms). The dialog system may dynamically engage in a conversation with the client using a dialog system, or alternative the questions can be reviewed and used by a domain expert. The present invention may analyse the responses/answers provided by the client in order to trigger a next relevant question and collects the evidence needed to assess the patient well-being of the client (e.g., difficulty to sleep or other symptoms of depression). As such, the present invention may also enhance, supplement, and/or fill in data (e.g., missing patient information) a domain expert may need to be aware of for further analysis. The present invention learns which questions have been proven to be beneficial in a given context. This way, question generation can further be optimized.

The present invention may provide positive evidence and/or negative evidence from the domain knowledge and machine learning (in addition to the historical data) by engaging in a dialog/conversation with the client (e.g., performing an active learning operation). The present invention may incorporate the answers provided in the dialog given by clients to obtain (e.g., re-rank) and present the optimal evidence as well as to augment a knowledge base and/or domain knowledge with the new information, which may previously be missing, absent, and/or incomplete. The collected feedback may include updated information that may be missing from a knowledge base and/or domain knowledge. A machine learning mechanism may use the heterogeneous historical input and/or feedback information to build customized questionnaire from dynamically generated customized question provided by the dialog system based on each respective response/answer to a previous question/query.

In one aspect, the health state (e.g., wellness) may include at least one or more medical conditions of one or more clients, a health state (e.g., subjective health state "SWB", emotional health state, mental health state, physical health state, or an overall health state) of the one or more clients, an emotional state of the one or more clients, biometric data, behavior patterns, a health profile of the client, or a combination thereof. In one aspect, health state may be generally described as a normal/standardized or satisfactory condition of existence of the client or a state characterized by health, happiness, emotional stability, mental stability, physical stability, or success. As one of ordinary skill in the art will appreciate, "health state" may be dependent on a number of factors, including such factors as medical condition, emotional stability, mental stability, physical stability, financial stability, a degree or level of happiness, or other factors that may be learned. A health state of a client/patient may be defined. For example, a knowledge base or ontology may be used to define a health state for a client/patient and may include defining and/or indicating one or more correlations between a health state, a plurality of states, medical conditions, activities of daily living (ADL), and context of daily living (CDL).

Moreover, as used herein, ADLs may refer to the most common activities that people perform during a day. For example, activities of daily living may include many activities that take place throughout the day, particularly going to work, child-care, elderly care, health management, communication management, financial management, safety/emergency responses, shopping, visiting friends or family, traveling, housekeeping, grooming or personal hygiene practices, meal preparation/dining out, engaging in social media, and even using a computer. ADLs may also be used in terms of healthcare to refer to the person's daily self-care activities. The context of daily living ("CDL" or "CDLs") may refer to the context in which one or more ADLs are executed or carried out. The CDL may also include one or more dimensions such as, for example, time, location, environment conditions, weather conditions, traffic conditions, and the like. A domain knowledge may provide one or more correlations or relationships between a person's health state and the ADLs and CDLs.

Some ADLs may also be applicable for one or more types of specific events. For example, a person having experienced a recent surgical procedure may require different or altered ADLs for treatment, recovery, or even resuming previously enjoyed ADLs. Each organism (e.g., person) may have different ADLs than other persons. Accordingly, the ADLs for each person may be learned, identified, and analyzed. In one aspect, the ADLs for a person may be learned such as, for example, using machine learning or using a domain knowledge relating to information about the person's activities and behaviors, which may be stored in a patient profile.

It should be noted as described herein, the term "cognitive" (or "cognition") may be relating to, being, or involving conscious intellectual activity such as, for example, thinking, reasoning, or remembering, that may be performed using machine learning. In an additional aspect, cognitive or "cognition" may be the mental process of knowing, including aspects such as awareness, perception, reasoning and judgment. A machine learning system may use artificial reasoning to interpret data from one or more data sources (e.g., sensor-based devices or other computing systems) and learn topics, concepts, and/or processes that may be determined and/or derived by machine learning.

In an additional aspect, cognitive or "cognition" may refer to a mental action or process of acquiring knowledge and understanding through thought, experience, and one or more senses using machine learning (which may include using sensor-based devices or other computing systems that include audio or video devices). Cognitive may also refer to identifying patterns of behavior, leading to a "learning" of one or more problems, domains, events, operations, or processes. Thus, the cognitive model may, over time, develop semantic labels to apply to observed behavior, domains, problems, and use a domain knowledge or ontology to store the learned observed behavior, problems, and domain. In one embodiment, the system provides for progressive levels of complexity in what may be learned from the one or more dialogs, operations, or processes.

In an additional aspect, the term cognitive may refer to a cognitive system. The cognitive system may be a specialized computer system, or set of computer systems, configured with hardware and/or software logic (in combination with hardware logic upon which the software executes) to emulate human cognitive functions. These cognitive systems apply human-like characteristics to convey and manipulate ideas which, when combined with the inherent strengths of digital computing, can solve problems with a high degree of accuracy (e.g., within a defined percentage range or above an accuracy threshold) and resilience on a large scale. A cognitive system may perform one or more computer-implemented cognitive operations that approximate a human thought process while enabling a client or a computing system to interact in a more natural manner. A cognitive system may comprise artificial intelligence logic, such as natural language processing (NLP) based logic, for example, and machine learning logic, which may be provided as specialized hardware, software executed on hardware, or any combination of specialized hardware and software executed on hardware. The logic of the cognitive system may implement the cognitive operation(s), examples of which include, but are not limited to, question answering, identifying problems, identification of related concepts within different portions of content in a corpus, and intelligent search algorithms, such as Internet web page searches.

In general, such cognitive systems are able to perform the following functions: 1) Navigate the complexities of human language and understanding; 2) Ingest and process vast amounts of structured and unstructured data; 3) Generate and evaluate hypotheses; 4) Weigh and evaluate responses that are based only on relevant evidence; 5) Provide situation-specific advice, insights, estimations, determinations, evaluations, calculations, and guidance; 6) Improve knowledge and learn with each iteration and interaction through machine learning processes; 7) Enable decision making at the point of impact (contextual guidance); 8) Scale in proportion to a task, process, or operation; 9) Extend and magnify human expertise and cognition; 10) Identify resonating, human-like attributes and traits from natural language; 11) Deduce various language specific or agnostic attributes from natural language; 12) Memorize and recall relevant data points (images, text, voice) (e.g., a high degree of relevant recollection from data points (images, text, voice) (memorization and recall)); and/or 13) Predict and sense with situational awareness operations that mimic human cognition based on experiences.

It should be noted that a cognitive system may also perform one or more calculations that may be performed using various mathematical operations or functions that may involve one or more mathematical operations (e.g., solving differential equations or partial differential equations analytically or computationally, using addition, subtraction, division, multiplication, standard deviations, means, averages, percentages, statistical modeling using statistical distributions, by finding minimums, maximums or similar thresholds for combined variables, etc.).

Other examples of various aspects of the illustrated embodiments, and corresponding benefits, will be described further herein.

It is understood in advance that although this disclosure includes a detailed description on cloud computing, implementation of the teachings recited herein are not limited to a cloud computing environment and/or computing systems associated with one or more medium/means. Rather, embodiments of the present invention are capable of being implemented in conjunction with any other type of computing environment now known or later developed.

Cloud computing is a model of service delivery for enabling convenient, on-demand network access to a shared pool of configurable computing resources (e.g., networks, network bandwidth, servers, processing, memory, storage, applications, virtual machines, and services) that can be rapidly provisioned and released with minimal management effort or interaction with a provider of the service. This cloud model may include at least five characteristics, at least three service models, and at least four deployment models.

Characteristics are as follows:

On-demand self-service: a cloud consumer can unilaterally provision computing capabilities, such as server time and network storage, as needed automatically without requiring human interaction with the service's provider.

Broad network access: capabilities are available over a network and accessed through standard mechanisms that promote use by heterogeneous thin or thick client platforms (e.g., mobile phones, laptops, and PDAs).

Resource pooling: the provider's computing resources are pooled to serve multiple consumers using a multi-tenant model, with different physical and virtual resources dynamically assigned and reassigned according to demand. There is a sense of location independence in that the consumer generally has no control or knowledge over the exact location of the provided resources but may be able to specify location at a higher level of abstraction (e.g., country, state, or datacenter).

Rapid elasticity: capabilities can be rapidly and elastically provisioned, in some cases automatically, to quickly scale out and rapidly released to quickly scale in. To the consumer, the capabilities available for provisioning often appear to be unlimited and can be purchased in any quantity at any time.

Measured service: cloud systems automatically control and optimize resource use by leveraging a metering capability at some level of abstraction appropriate to the type of service (e.g., storage, processing, bandwidth, and active client accounts). Resource usage can be monitored, controlled, and reported providing transparency for both the provider and consumer of the utilized service.

Service Models are as follows:

Software as a Service (SaaS): the capability provided to the consumer is to use the provider's applications running on a cloud infrastructure. The applications are accessible from various client devices through a thin client interface such as a web browser (e.g., web-based e-mail). The consumer does not manage or control the underlying cloud infrastructure including network, servers, operating systems, storage, or even individual application capabilities, with the possible exception of limited client-specific application configuration settings.

Platform as a Service (PaaS): the capability provided to the consumer is to deploy onto the cloud infrastructure consumer-created or acquired applications created using programming languages and tools supported by the provider. The consumer does not manage or control the underlying cloud infrastructure including networks, servers, operating systems, or storage, but has control over the deployed applications and possibly application hosting environment configurations.

Infrastructure as a Service (IaaS): the capability provided to the consumer is to provision processing, storage, networks, and other fundamental computing resources where the consumer is able to deploy and run arbitrary software, which can include operating systems and applications. The consumer does not manage or control the underlying cloud infrastructure but has control over operating systems, storage, deployed applications, and possibly limited control of select networking components (e.g., host firewalls).

Deployment Models are as follows:

Private cloud: the cloud infrastructure is operated solely for an organization. It may be managed by the organization or a third party and may exist on-premises or off-premises.

Community cloud: the cloud infrastructure is shared by several organizations and supports a specific community that has shared concerns (e.g., mission, security requirements, policy, and compliance considerations). It may be managed by the organizations or a third party and may exist on-premises or off-premises.

Public cloud: the cloud infrastructure is made available to the general public or a large industry group and is owned by an organization selling cloud services.

Hybrid cloud: the cloud infrastructure is a composition of two or more clouds (private, community, or public) that remain unique entities but are bound together by standardized or proprietary technology that enables data and application portability (e.g., cloud bursting for load-balancing between clouds).

A cloud computing environment is service oriented with a focus on statelessness, low coupling, modularity, and semantic interoperability. At the heart of cloud computing is an infrastructure comprising a network of interconnected nodes.

Referring now to FIG. 1, a schematic of an example of a cloud computing node is shown. Cloud computing node 10 is only one example of a suitable cloud computing node and is not intended to suggest any limitation as to the scope of use or functionality of embodiments of the invention described herein. Regardless, cloud computing node 10 is capable of being implemented and/or performing any of the functionality set forth hereinabove.

In cloud computing node 10 there is a computer system/server 12, which is operational with numerous other general purpose or special purpose computing system environments or configurations. Examples of well-known computing systems, environments, and/or configurations that may be suitable for use with computer system/server 12 include, but are not limited to, personal computer systems, server computer systems, thin clients, thick clients, hand-held or laptop devices, multiprocessor systems, microprocessor-based systems, set top boxes, programmable consumer electronics, network PCs, minicomputer systems, mainframe computer systems, and distributed cloud computing environments that include any of the above systems or devices, and the like.

Computer system/server 12 may be described in the general context of computer system-executable instructions, such as program modules, being executed by a computer system. Generally, program modules may include routines, programs, objects, components, logic, data structures, and so on that perform particular tasks or implement particular abstract data types. Computer system/server 12 may be practiced in distributed cloud computing environments where tasks are performed by remote processing devices that are linked through a communications network. In a distributed cloud computing environment, program modules may be located in both local and remote computer system storage media including memory storage devices.

As shown in FIG. 1, computer system/server 12 in cloud computing node 10 is shown in the form of a general-purpose computing device. The components of computer system/server 12 may include, but are not limited to, one or more processors or processing units 16, a system memory 28, and a bus 18 that couples various system components including system memory 28 to processor 16.

Bus 18 represents one or more of any of several types of bus structures, including a memory bus or memory controller, a peripheral bus, an accelerated graphics port, and a processor or local bus using any of a variety of bus architectures. By way of example, and not limitation, such architectures include Industry Standard Architecture (ISA) bus, Micro Channel Architecture (MCA) bus, Enhanced ISA (EISA) bus, Video Electronics Standards Association (VESA) local bus, and Peripheral Component Interconnects (PCI) bus.

Computer system/server 12 typically includes a variety of computer system readable media. Such media may be any available media that is accessible by computer system/server 12, and it includes both volatile and non-volatile media, removable and non-removable media.

System memory 28 can include computer system readable media in the form of volatile memory, such as random access memory (RAM) 30 and/or cache memory 32. Computer system/server 12 may further include other removable/non-removable, volatile/non-volatile computer system storage media. By way of example only, storage system 34 can be provided for reading from and writing to a non-removable, non-volatile magnetic media (not shown and typically called a "hard drive"). Although not shown, a magnetic disk drive for reading from and writing to a removable, non-volatile magnetic disk (e.g., a "floppy disk"), and an optical disk drive for reading from or writing to a removable, non-volatile optical disk such as a CD-ROM, DVD-ROM or other optical media can be provided. In such instances, each can be connected to bus 18 by one or more data media interfaces. As will be further depicted and described below, system memory 28 may include at least one program product having a set (e.g., at least one) of program modules that are configured to carry out the functions of embodiments of the invention.

Program/utility 40, having a set (at least one) of program modules 42, may be stored in system memory 28 by way of example, and not limitation, as well as an operating system, one or more application programs, other program modules, and program data. Each of the operating system, one or more application programs, other program modules, and program data or some combination thereof, may include an implementation of a networking environment. Program modules 42 generally carry out the functions and/or methodologies of embodiments of the invention as described herein.

Computer system/server 12 may also communicate with one or more external devices 14 such as a keyboard, a pointing device, a display 24, etc.; one or more devices that enable a client to interact with computer system/server 12; and/or any devices (e.g., network card, modem, etc.) that enable computer system/server 12 to communicate with one or more other computing devices. Such communication can occur via Input/Output (I/O) interfaces 22. Still yet, computer system/server 12 can communicate with one or more networks such as a local area network (LAN), a general wide area network (WAN), and/or a public network (e.g., the Internet) via network adapter 20. As depicted, network adapter 20 communicates with the other components of computer system/server 12 via bus 18. It should be understood that although not shown, other hardware and/or software components could be used in conjunction with computer system/server 12. Examples include, but are not limited to: microcode, device drivers, redundant processing units, external disk drive arrays, RAID systems, tape drives, and data archival storage systems, etc.

Figure 2:
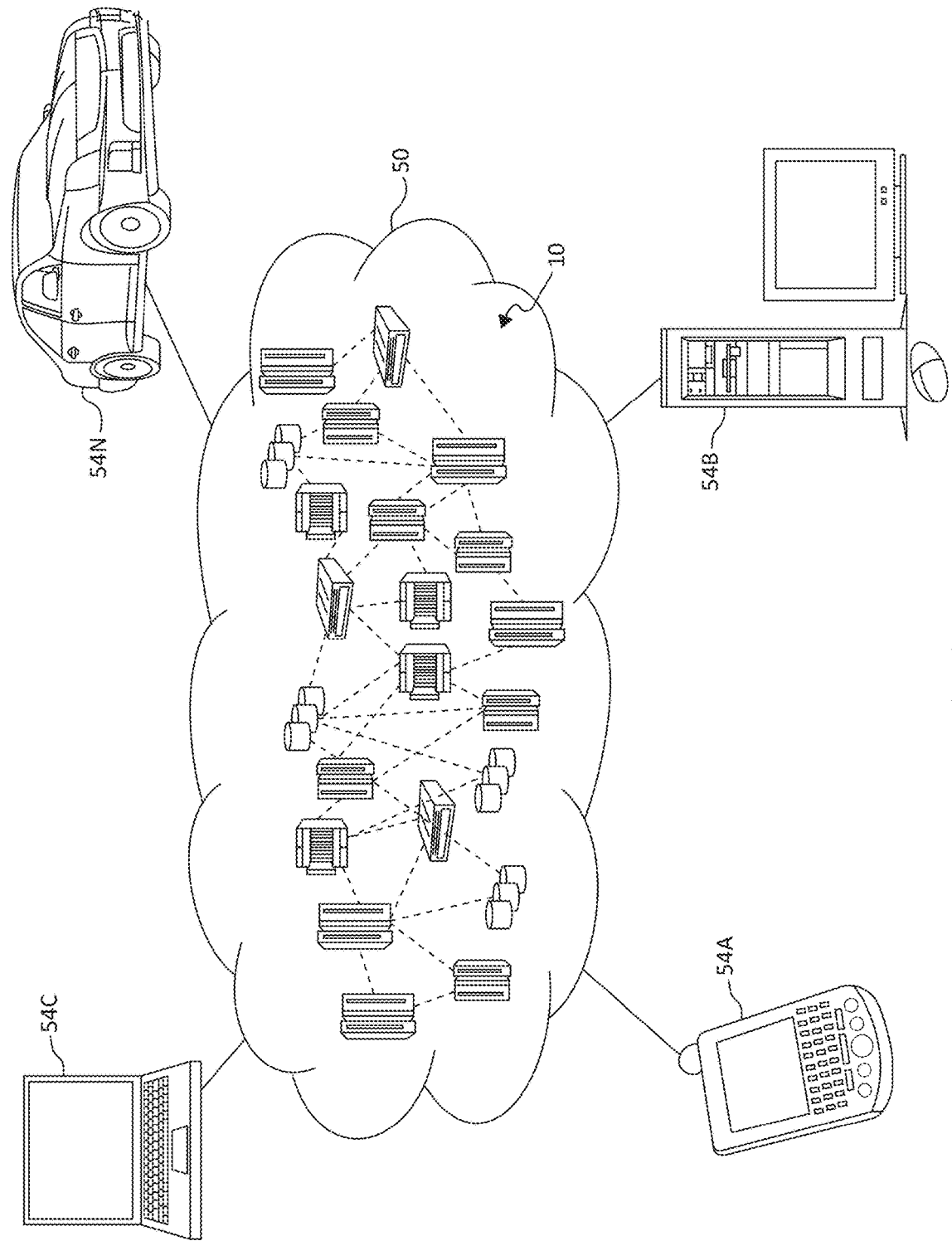
FIG. 2 is an additional block diagram depicting an exemplary cloud computing environment according to an embodiment of the present invention.

Referring now to FIG. 2, illustrative cloud computing environment 50 is depicted. As shown, cloud computing environment 50 comprises one or more cloud computing nodes 10 with which local computing devices used by cloud consumers, such as, for example, personal digital assistant (PDA) or cellular telephone 54A, desktop computer 54B, laptop computer 54C, and/or computer system 54N may communicate. Nodes 10 may communicate with one another. They may be grouped (not shown) physically or virtually, in one or more networks, such as Private, Community, Public, or Hybrid clouds as described hereinabove, or a combination thereof. This allows cloud computing environment 50 to offer infrastructure, platforms and/or software as services for which a cloud consumer does not need to maintain resources on a local computing device. It is understood that the types of computing devices 54A-N shown in FIG. 2 are intended to be illustrative only and that computing nodes 10 and cloud computing environment 50 can communicate with any type of computerized device over any type of network and/or network addressable connection (e.g., using a web browser).

Figure 3:
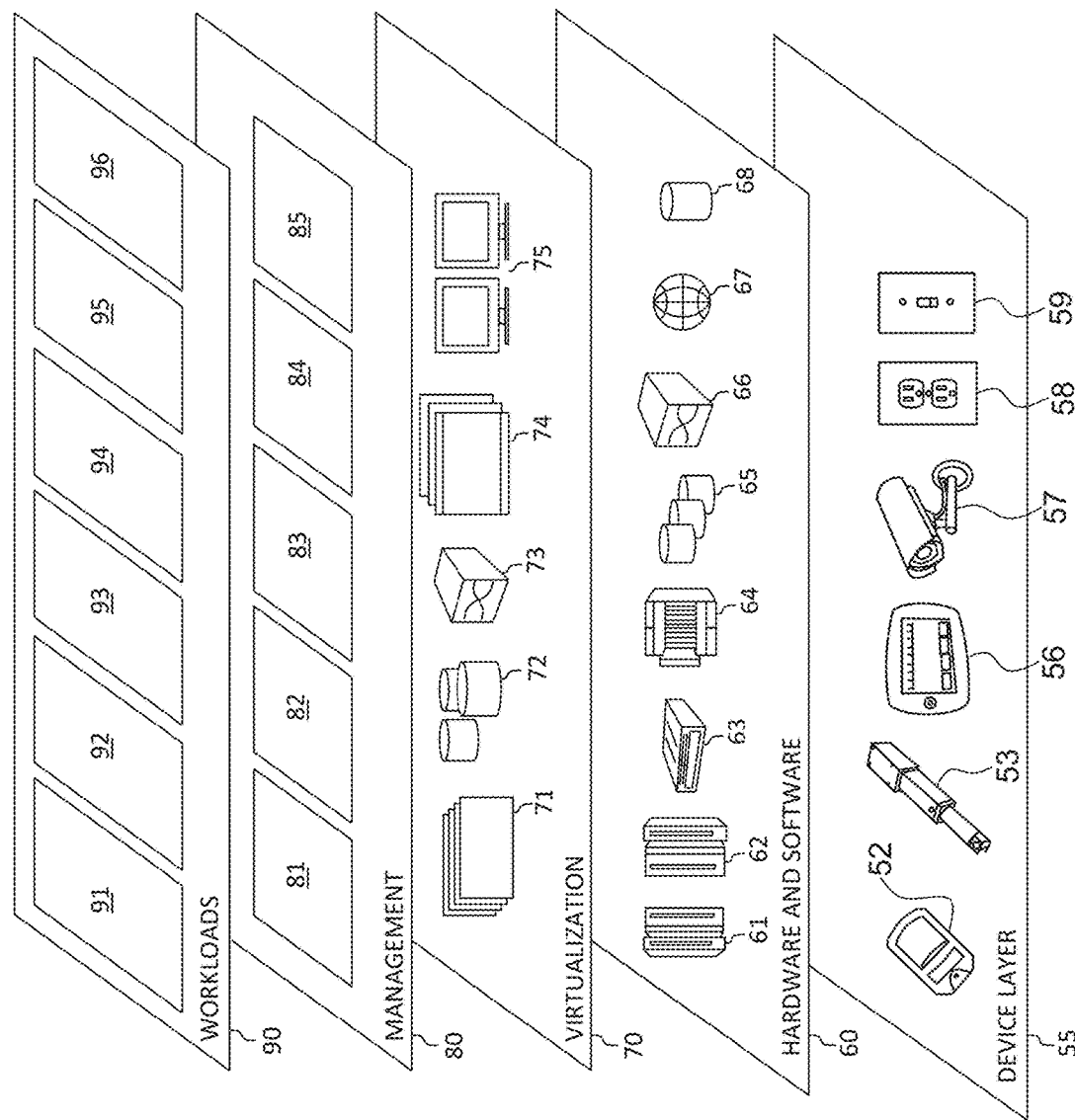
FIG. 3 is an additional block diagram depicting abstraction model layers according to an embodiment of the present invention.

Referring now to FIG. 3, a set of functional abstraction layers provided by cloud computing environment 50 (FIG. 2) is shown. It should be understood in advance that the components, layers, and functions shown in FIG. 3 are intended to be illustrative only and embodiments of the invention are not limited thereto. As depicted, the following layers and corresponding functions are provided:

Device layer 55 includes physical and/or virtual devices, embedded with and/or standalone electronics, sensors, actuators, and other objects to perform various tasks in a cloud computing environment 50. Each of the devices in the device layer 55 incorporates networking capability to other functional abstraction layers such that information obtained from the devices may be provided thereto, and/or information from the other abstraction layers may be provided to the devices. In one embodiment, the various devices inclusive of the device layer 55 may incorporate a network of entities collectively known as the "internet of things" (IoT). Such a network of entities allows for intercommunication, collection, and dissemination of data to accomplish a great variety of purposes, as one of ordinary skill in the art will appreciate.

Device layer 55 as shown includes sensor 52, actuator 53, "learning" thermostat 56 with integrated processing, sensor, and networking electronics, camera 57, controllable household outlet/receptacle 58, and controllable electrical switch 59 as shown. Other possible devices may include, but are not limited to various additional sensor devices, networking devices, electronics devices (such as a remote-control device), additional actuator devices, so called "smart" appliances such as a refrigerator or washer/dryer, and a wide variety of other possible interconnected objects.

Hardware and software layer 60 includes hardware and software components. Examples of hardware components include: mainframes 61; RISC (Reduced Instruction Set Computer) architecture based servers 62; servers 63; blade servers 64; storage devices 65; and networks and networking components 66. In some embodiments, software components include network application server software 67 and database software 68.

Virtualization layer 70 provides an abstraction layer from which the following examples of virtual entities may be provided: virtual servers 71; virtual storage 72; virtual networks 73, including virtual private networks; virtual applications and operating systems 74; and virtual clients 75.

In one example, management layer 80 may provide the functions described below. Resource provisioning 81 provides dynamic procurement of computing resources and other resources that are utilized to perform tasks within the cloud computing environment. Metering and Pricing 82 provides cost tracking as resources are utilized within the cloud computing environment, and billing or invoicing for consumption of these resources. In one example, these resources may comprise application software licenses. Security provides identity verification for cloud consumers and tasks, as well as protection for data and other resources. Client portal 83 provides access to the cloud computing environment for consumers and system administrators. Service level management 84 provides cloud computing resource allocation and management such that required service levels are met. Service Level Agreement (SLA) planning and fulfillment 85 provides pre-arrangement for, and procurement of, cloud computing resources for which a future requirement is anticipated in accordance with an SLA.

Workloads layer 90 provides examples of functionality for which the cloud computing environment may be utilized. Examples of workloads and functions which may be provided from this layer include: mapping and navigation 91;

software development and lifecycle management 92; virtual classroom education delivery 93; data analytics processing 94; transaction processing 95; and, in the context of the illustrated embodiments of the present invention, various workloads and functions 96 for intelligent generation of a customized questionnaire. In addition, workloads and functions 96 for intelligent generation of a customized questionnaire may include such operations as data analytics, data analysis, and as will be further described, notification functionality. One of ordinary skill in the art will appreciate that the workloads and functions 96 for intelligent generation of a customs questionnaire may also work in conjunction with other portions of the various abstraction layers, such as those in hardware and software 60, virtualization 70, management 80, and other workloads 90 (such as data analytics processing 94, for example) to accomplish the various purposes of the illustrated embodiments of the present invention.

As previously mentioned, the mechanisms of the illustrated embodiments provide novel approaches for a cognitive system that provides intelligent generation of a customized questionnaire. These mechanisms include functionality that use as input into the cognitive system 1) a domain knowledge (e.g., a knowledge base with data records and historical data), 2) client profiles, 3) interactions between a client and alternative clients (e.g., family members, friends, co-workers, social media peers/associates, 4) goals/expected outcomes, and/or 5) one or more existing/previous questions and questionnaires and responses/answers to various queries and additional feedback. Using the collected input data, the cognitive system may generate/build questions and/or select questions from previous interactions with similar clients (e.g., patients, etc.) and/or identify/determine one or more relevant questions to include in questionnaire. The intelligent system may provide evidence for each question (e.g., set of facts, reasoning, and/or hypotheses, etc.). One or more queries/questions may be issued/asked to one or more clients (e.g., doctor, patient, domain expert) to fill in any missing, uncertain, and/or incomplete information relating to the client and/or client responses (e.g., to validate the explanations and augment the knowledge base/domain knowledge if the knowledge base/domain knowledge is insufficient to generate a complete and/or complete explanation with a certain confidence). The intelligent system may use the additional knowledge to improve the knowledge base(s), either by adding new questions and/or by updating existent questionnaires (e.g., existent questions or relations in the knowledge base and/or in the clinical data) if the existent relations were (partially) outdated or invalid.

Figure 4:
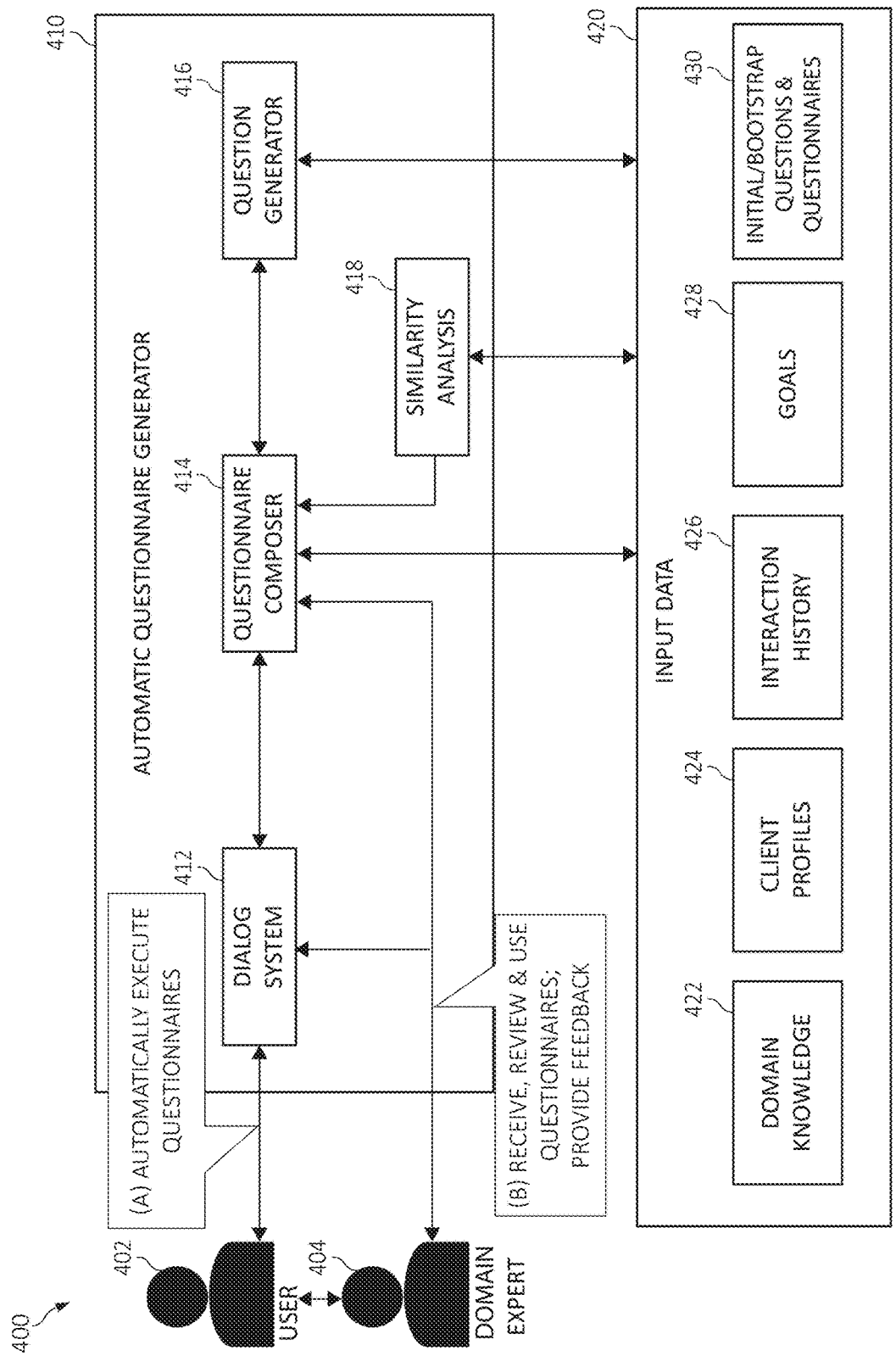
FIG. 4 is an additional block diagram depicting an exemplary functional relationship between various aspects of the present invention.

Turning now to FIG. 4, a block flow diagram depicting exemplary functional components 400 according to various mechanisms of the illustrated embodiments is shown. FIG. 4 illustrates intelligent generation of customized questionnaire workloads and functions in a computing environment, according to an example of the present technology. As will be seen, many of the functional blocks may also be considered "modules" or "components" of functionality, in the same descriptive sense as has been previously described in FIGS. 1-3.

With the foregoing in mind, the module/component blocks of computing system 400 (e.g., an intelligent/cognitive system) may also be incorporated into various hardware and software components of a system for intelligent learning for explaining anomalies in accordance with the present invention. Many of the functional blocks 400 may execute as background processes on various components, either in distributed computing components, or on the client device, or elsewhere.

The computing system 400 may include automatic questionnaire generator 410, which may also be included in and/or associated with the computer system/server 12 of FIG. 1. The automatic questionnaire generator 410 may include a dialog system 412, a questionnaire composer 414, and a question generator 416. The automatic questionnaire generator 410 may be in association with a domain knowledge 422, one or more client profiles 424, an interaction history 426 (e.g., history interaction between a defined client and other clients), goals 428 (e.g., health state/wellness goals), and/or initial/bootstrap questions & questionnaires (e.g., existing questions and/or questionnaires). That is, the interaction history 426 may refer to historical interactions with domain experts and/or clients (e.g., patients) using previously generated questionnaires such as, for example, by actively learning if the questions are relevant for a given context based on collected feedback. Collected feedback may include both explicit feedback from domain experts, and various forms of implicit feedback. Examples of implicit feedback may include identifying questions skipped by either the client or the domain expert.

The automatic questionnaire generator 410 may include a machine learning component and perform one or more various types of machine learning/deep learning operations such as, for example, artificial intelligence ("AI"), natural language processing ("NLP"), speech to text ("STT"), text to speech ("TTS"), or other type of deep learning operation.

The dialog system 412 may be a chatbot used to interact with the one or more clients such as, for example, clients 402 (e.g., patients, healthcare employees, business entity professionals/customers, etc.) and/or domain expert 404 (e.g., front end) and gather the information needed by the components of the automatic questionnaire generator 410 and/or receiving the input data 420.

That is, the dialog system 412 may interact with a client 402 by asking questions and receive answers to fill in gaps in client data and identify next steps. In one aspect, the only interaction with the client 402 may be for purposes of clarifying questions to resolve uncertainties. Also, feedback of a domain expert (e.g., domain expert 404) may be collected by the automatic questionnaire generator 410. However, all or portions of this feedback may also be specifically collected using the dialog system 412.

The questionnaire composer 414 may assemble a series/flow of questions (questionnaire) needed to obtain detailed, relevant, and/or meaningful information from the client 402 in a human-consumable format. The series/flow of questions may be modified based on the client's 402 answers to a previous question and/or series of questions. The questionnaire composer 414 may use the output of the question generator 416 and the similarity analysis 418 components to build, generate, create, the series/flow of questions that maximizes the probability of collecting an intended/desired information from the client 402 (e.g., patient, business/marking entity/customer).

In one aspect, the question generator 416 may provide arguments (e.g., positive evidence and/or negative evidence) to provide positive or negative support/reasons for the customized questions. The arguments may provide the base data (e.g., raw material/information) to build, generate, create, and/or re-generate the customized questions.

The similarity analysis 418 component may perform an analysis on the input data 420 and clustering of clients (e.g., patients) based on relevant features such as, for example, using K-means. In one aspect, the similarity analysis 418 component may perform the similarity analysis that may be inconclusive for the client 402 (e.g., mixed membership in more than one existing group) and thereby generate one or more intermediate questions with the intent of decreasing the inconclusive uncertainty. If a similarity analysis concludes that client 402 belongs to several clusters (e.g., one or more existing groups of clients), the similarity analysis may result in conflicting or inconclusive evidence. To resolve uncertainty, one or more intermediate questions may be generated. In one aspect, the similarity analysis 418 may use the input data (e.g., the domain knowledge 422 (e.g., structured and/or unstructured data) to generate one or more possible/potential explanations. In another aspect, the similarity analysis 418 may use a clustering operation (for example, K-Means clustering or a variation thereof and/or any other suitable clustering operation).

The question generator 415 may generate one or more customized questions and provide the customized questions in a natural language format that may be tailored to the client 402 (e.g., a current patient). The question generator 415 may use a combination of operations such as, for example, collaborative filtering, generating positive and/or negative evidence to extract detailed, relevant, and/or meaningful information pertaining to the client 402.

In one aspect, domain knowledge 422 may include structured data, such as, for example, knowledge graphs, various models (e.g., list of drugs, treatments and/or side effects, etc.), unstructured data such as, for example, books and scientific literature, etc. In one aspect, the domain knowledge 422 may be an ontology of concepts representing a domain of knowledge. A thesaurus or ontology may be used as the domain knowledge 422. In one aspect, the term "domain" is a term intended to have its ordinary meaning. In addition, the term "domain" may include an area of expertise for a system or a collection of material, information, content and/or other resources related to a particular subject or subjects. A domain can refer to information related to any particular subject matter or a combination of selected subjects.

Additionally, the client profiles 424 may include structured and/or unstructured data describing the patients pool. In one aspect, for example, the client profiles 424 may include data relating to each client (e.g., patient) such as, for example, health state data (e.g., ADLs, CDLs, emotional/physical/mental conditions, medical symptoms/conditions, medical treatments, biomedical data, electronic medical records ("EMRs"), etc.) employment data, priorities, activity preferences, daily or future calendaring information, behaviors, skill sets of a client, capabilities, performance capabilities, historical data, preferences, priorities, and the like. That is, the client profiles 424 may include also include data records and historical data (e.g., EMR clinical history or other relevant contextual history such as, for example, activities of daily living ("ADLs"), exercise, diet, sex, gender, other demographics, social determinants, etc., for all clients (historical clients) and the current clients).

The interaction history 426 may include historical data and/or collected feedback (e.g., feedback from the client 402 and/or the domain expert 404), questions and questionnaire recommended for other clients, answers/responses provided by other clients, previous answers from the clients.

The goals 428 may be a set of desired outcomes for a client 402 that may be specified by the domain expert 404 (e.g., a health state/wellness goal programs or improved/new ADLs or CDLs, performance/skill improvements, etc.).

The initial/bootstrap questions & questionnaires 430 (e.g., existing questions and/or questionnaires) may include an initial set of data to be used at bootstrap (e.g., the automatic questionnaire generator 410 system may use the initial/bootstrap questions & questionnaires 430 which may include a set of pre-existing/pre-defined and/or historical questions to bootstrap the process of questionnaire generations and/or learn and create new questions/questionnaires).

More specifically, the automatic questionnaire generator 410 (e.g., the dialog system 412, the questionnaire composer 414, and/or the question generator 416) may employ machine learning operations to perform one or more machine learning operations for generating the customized questionnaire. The automatic questionnaire generator 410 may use one or more machine learning operations to engage and/or communicate with the dialog system 412. In one aspect, the dialog system 412 may be chatbot used to interact with the one or more clients or domain experts such as, for example, clients 402 and/or the domain expert 404 (e.g., front end) and gather the information needed by a learning component (not shown for illustrative convenience) of the dialog system 450.

The dialog system 412 to may be used to query/ask questions to one or more clients such as, for example user 402 and/or domain expert 404, needed to fill in any knowledge gaps in in the client data. The acquired knowledge from the dialog system 450 may be used to enhance the current domain knowledge 422 and the client profiles 424. Also, the dialog system 412 may receive feedback data from domain expert 404 (e.g., a doctor or patient) and/or client 402 for acquiring additional knowledge. The dialog system 450 may provide the acquired data (e.g., feedback/answers to each query) to the active learning component 436, which may be then passed on and shared with the domain knowledge 422.

In one aspect, the machine learning modeling and/or operations, as described herein, may be performed using a wide variety of methods or combinations of methods, such as supervised learning, unsupervised learning, temporal difference learning, reinforcement learning and so forth. Some non-limiting examples of supervised learning which may be used with the present technology include AODE (averaged one-dependence estimators), artificial neural network, backpropagation, Bayesian statistics, naïve bayes classifier, Bayesian network, Bayesian knowledge base, case-based reasoning, decision trees, inductive logic programming, Gaussian process regression, gene expression programming, group method of data handling (GMDH), learning automata, learning vector quantization, minimum message length (decision trees, decision graphs, etc.), lazy learning, instance-based learning, nearest neighbor algorithm, analogical modeling, probably approximately correct (PAC) learning, ripple down rules, a knowledge acquisition methodology, symbolic machine learning algorithms, sub symbolic machine learning algorithms, support vector machines, random forests, ensembles of classifiers, bootstrap aggregating (bagging), boosting (meta-algorithm), ordinal classification, regression analysis, information fuzzy networks (IFN), statistical classification, linear classifiers, fisher's linear discriminant, logistic regression, perceptron, support vector machines, quadratic classifiers, k-nearest neighbor, hidden Markov models and boosting. Some non-limiting examples of unsupervised learning which may be used with the present technology include artificial neural network, data clustering, expectation-maximization, self-organizing map, radial basis function network, vector quantization, generative topographic map, information bottleneck method, IBSEAD (distributed autonomous entity systems based interaction), association rule learning, apriori algorithm, eclat algorithm, FP-growth algorithm, hierarchical clustering, single-linkage clustering, conceptual clustering, partitional clustering, k-means algorithm, fuzzy clustering, and reinforcement learning. Some non-limiting example of temporal difference learning may include Q-learning and learning automata. Specific details regarding any of the examples of supervised, unsupervised, temporal difference or other machine learning described in this paragraph are known and are within the scope of this disclosure. Also, when deploying one or more machine learning models, a computing device may be first tested in a controlled environment before being deployed in a public setting. Also even when deployed in a public environment (e.g., external to the controlled, testing environment), the computing devices may be monitored for compliance.

Figure 5:
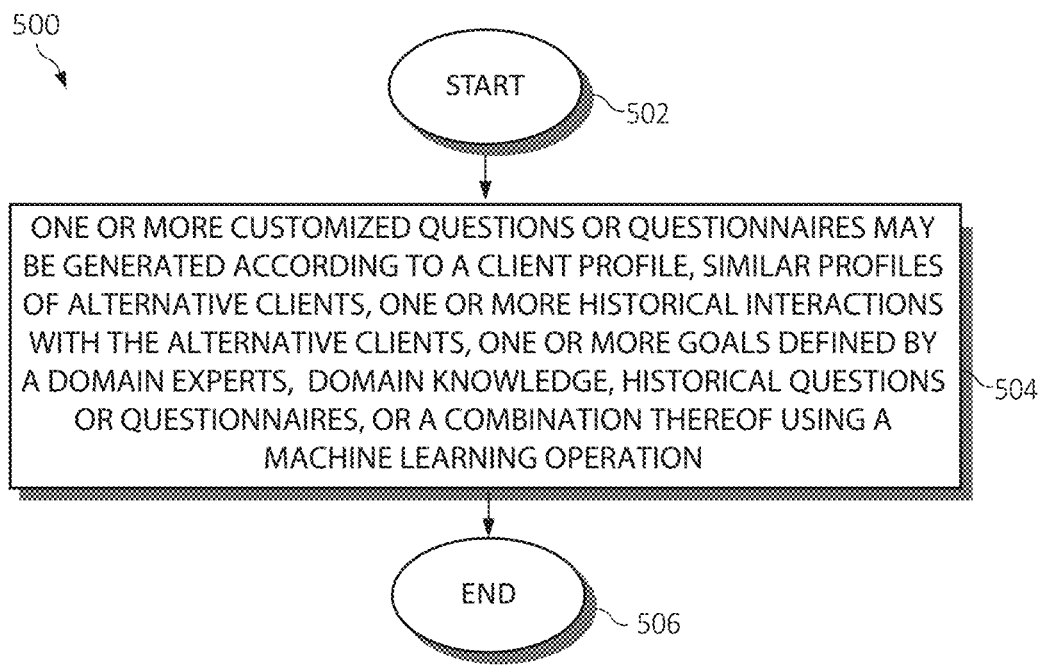
FIG. 5 is a flowchart diagram depicting an exemplary method for intelligent generation of customized questions in which aspects of the present invention may be realized.

Turning now to FIG. 5, a method 500 for implementing intelligent generation of customized questions or questionnaires by a processor is depicted, in which various aspects of the illustrated embodiments may be implemented. The functionality 500 may be implemented as a method executed as instructions on a machine, where the instructions are included on at least one computer readable medium or one non-transitory machine-readable storage medium. The functionality 500 may start in block 502.

One or more customized questions or questionnaires may be generated according to a client profile, similar profiles of alternative clients, one or more historical interactions with the alternative clients, one or more goals defined by a domain experts, domain knowledge, historical (e.g., existing) questions or questionnaires, or a combination thereof using a machine learning operation, as in block 504. The functionality 500 may end, as in block 506.

Figure 6:
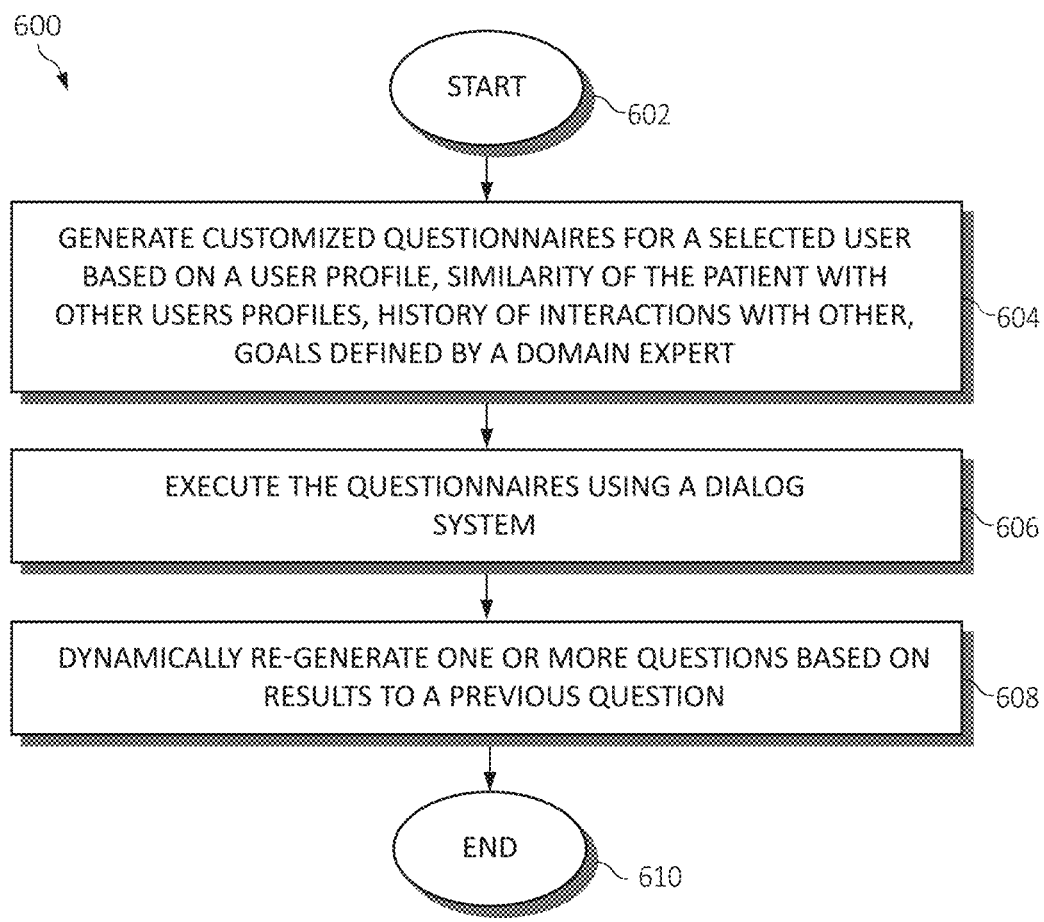
FIG. 6 is a flowchart diagram depicting an exemplary method for intelligent generation of a customized questions or questionnaires in which aspects of the present invention may be realized.

Turning now to FIG. 6, a method 600 for implementing intelligent generation of customized questions or questionnaires by a processor is depicted, in which various aspects of the illustrated embodiments may be implemented. The functionality 600 may be implemented as a method executed as instructions on a machine, where the instructions are included on at least one computer readable medium or one non-transitory machine-readable storage medium. The functionality 600 may start in block 602.

A customized questionnaire (e.g., a series of queries) may be generated for a selected user/client (e.g., a patient) based on a client profile (e.g., a patient profile), similarity of the user profile (e.g., client profile) with other user/client profiles, history of interactions with other users/clients, goals defined by a domain expert, as in block 604. The customized questionnaire may be executed using a dialog system (e.g., a plan-based dialog system/chatbot), as in block 606. One or more questions of the customized questionnaire may be dynamically re-generated based on results to one or more previous questions, as in block 608. The functionality 600 may end, as in block 610.

Figure 7:
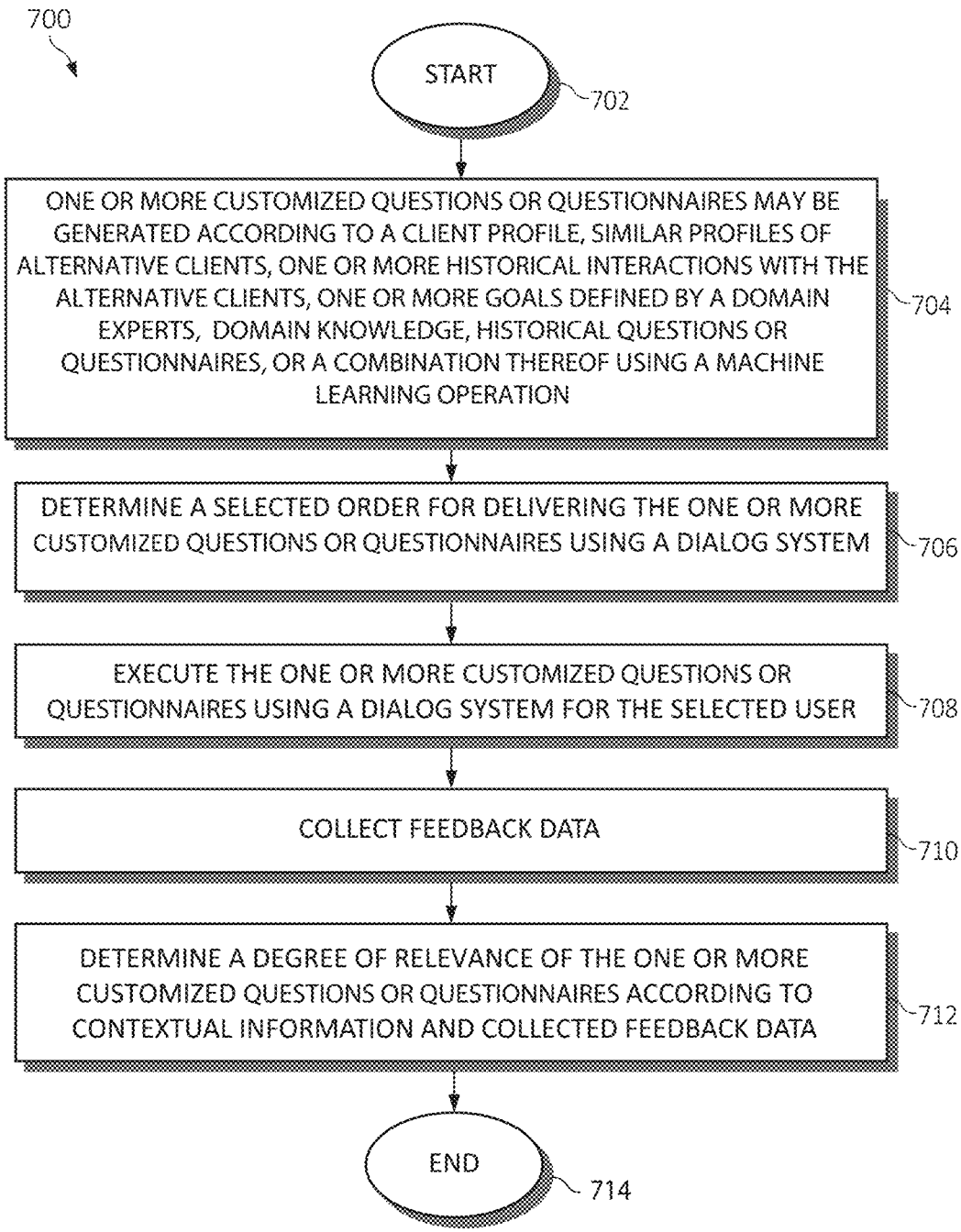
FIG. 7 is an additional flowchart diagram depicting an exemplary method for intelligent generation of a customized questions or questionnaires by a processor, again in which aspects of the present invention may be realized.

Turning now to FIG. 7, a method 700 for implementing intelligent generation of a customized questions (e.g., customized queries) or questionnaires (series of queries) by a processor is depicted, in which various aspects of the illustrated embodiments may be implemented. The functionality 700 may be implemented as a method executed as instructions on a machine, where the instructions are included on at least one computer readable medium or one non-transitory machine-readable storage medium. The functionality 700 may start in block 702.

One or more customized questions or questionnaires may be generated according to a client profile, similar profiles of alternative clients, one or more historical interactions with the alternative clients, one or more goals defined by a domain experts, domain knowledge, historical (e.g., existing) questions or questionnaires, or a combination thereof using a machine learning operation, as in block 704. A selected order for delivering the one or more customized questions or questionnaires using a dialog system may be determined, as in block 706. The one or more customized queries may be executed/performed using a dialog system for the selected client, as in block 708. Feedback data may be collected, as in block 710. A degree of relevance of the one or more customized questions or questionnaires may be determined according to contextual information nd collected feedback data, as in block 712. The functionality 700 may end, as in block 714.

The present invention may be a system, a method, and/or a computer program product. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punchcards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Smalltalk, C++ or the like, and conventional procedural programming languages, such as the "C" programming language or similar programming languages. The computer readable program instructions may execute entirely on the client's computer, partly on the client's computer, as a stand-alone software package, partly on the client's computer and partly on a remote computer or entirely on the remote computer or server. In the latter scenario, the remote computer may be connected to the client's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general-purpose computer, special purpose computer, or other programmable data processing apparatus to produce a machine, such that the instructions, which execute via the processor of the computer or other programmable data processing apparatus, create means for implementing the functions/acts specified in the flowcharts and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowcharts and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowcharts and/or block diagram block or blocks.

The flowcharts and block diagrams in the Figures illustrate the architecture, functionality, and operation of possible implementations of systems, methods, and computer program products according to various embodiments of the present invention. In this regard, each block in the flowcharts or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustrations, and combinations of blocks in the block diagrams and/or flowchart illustrations, can be implemented by special purpose hardware-based systems that perform the specified functions or acts or carry out combinations of special purpose hardware and computer instructions.

The invention claimed is:

1. A method for implementing intelligent generation of questions by a processor, comprising:
receiving, by a dialog system, data representative of a user profile, a domain knowledge, and historical questions associated with historical questionnaires for each of a plurality of users;
training, using one or more deep learning operations executed by machine learning logic, the dialog system to automatically and adaptively generate one or more customized questions or questionnaires using the data, wherein the training includes initially grouping each of the plurality of users into clusters according to characteristics identified in the data;
subsequent to initially grouping each of the plurality of users into the clusters, generating the one or more customized questions or questionnaires according to an analysis of the data, and to which of the clusters each of the plurality of users currently belongs, by the one or more deep learning operations in conjunction with one or more current responses to one or more current queries iteratively provided to a selected user by the dialog system subsequent to initially generating the one or more customized questions or questionnaires, wherein, the one or more customized questions or questionnaires are initially generated using only textual content of the data, and any spoken interaction comprising spoken utterances between the dialog system and the user subsequent to the initial generation and with respect to the one or more current queries is to resolve uncertainties in the data when generating further questions of the one or more customized questions or questionnaires for the user; and
responsive to the one or more current responses from the selected user yielding an inconclusive result that currently updates a placement of the selected user into conflicting clusters, dynamically updating the one or more customized questions or questionnaires in real time by automatically generating intermediate questions during the one or more current queries to resolve the inconclusive result and determine which of the clusters the selected user currently belongs prior to continuing with generating the one or more customized questions or questionnaires.

2. The method of claim 1, further including determining a selected order for delivering the one or more customized questions or questionnaires using a dialog system.

3. The method of claim 2, further including dynamically adjusting the selected order of the one or more customized questions or questionnaires according to a response provided to a previous query.

4. The method of claim 1, further including collecting feedback information relating to the one or more customized questions or questionnaires.

5. The method of claim 1, further including determining a degree of relevance of the one or more customized questions or questionnaires according to contextual information and collected feedback data.

6. The method of claim 1, further including initializing a machine learning mechanism to apply one or more machine learning models or rules to generate the one or more customized questions or questionnaires for the selected user, taking into account previously collected feedback, modify the one or more customized questions or questionnaires, learning customized questions pertaining to the similar profiles of the alternative users, analyze the one or more current responses to the one or more current queries, or perform a combination thereof.

7. A system for implementing intelligent generation of questions, comprising:
one or more computers with executable instructions that when executed cause the system to:
receive, by a dialog system, data representative of a user profile, a domain knowledge, and historical questions associated with historical questionnaires for each of a plurality of users;
train, using one or more deep learning operations executed by machine learning logic, the dialog system to automatically and adaptively generate one or more customized questions or questionnaires using the data, wherein the training includes initially grouping each of the plurality of users into clusters according to characteristics identified in the data;
subsequent to initially grouping each of the plurality of users into the clusters, generate the one or more customized questions or questionnaires according to an analysis of the data, and to which of the clusters each of the plurality of users currently belongs, by the one or more deep learning operations in conjunction with one or more current responses to one or more current queries iteratively provided to a selected user by the dialog system subsequent to initially generating the one or more customized questions or questionnaires, wherein, the one or more customized questions or questionnaires are initially generated using only textual content of the data, and any spoken interaction comprising spoken utterances between the dialog system and the user subsequent to the initial generation and with respect to the one or more current queries is to resolve uncertainties in the data when generating further questions of the one or more customized questions or questionnaires for the user; and
responsive to the one or more current responses from the selected user yielding an inconclusive result that currently updates a placement of the selected user into conflicting clusters, dynamically update the one or more customized questions or questionnaires in real time by automatically generating intermediate questions during the one or more current queries to resolve the inconclusive result and determine which of the clusters the selected user currently belongs prior to continuing with generating the one or more customized questions or questionnaires.

8. The system of claim 7, wherein the executable instructions further determine a selected order for delivering the one or more customized questions or questionnaires using a dialog system.

9. The system of claim 8, wherein the executable instructions further dynamically adjust the selected order of the one or more customized questions or questionnaires according to a response provided to a previous query.

10. The system of claim 7, wherein the executable instructions further collect feedback information relating to the one or more customized questions or questionnaires.

11. The system of claim 7, wherein the executable instructions further determine a degree of relevance of the one or more customized questions or questionnaires according to contextual information and collected feedback data.

12. The system of claim 7, wherein the executable instructions further initialize a machine learning mechanism to apply one or more machine learning models or rules to generate the one or more customized questions or questionnaires for the selected user, taking into account previously collected feedback, modify the one or more customized questions or questionnaires, learning customized questions pertaining to the similar profiles of the alternative users, analyze the one or more current responses to the one or more current queries, or perform a combination thereof.

13. A computer program product for implementing intelligent generation of questions by a processor, the computer program product comprising a non-transitory computer-readable storage medium having computer-readable program code portions stored therein, the computer-readable program code portions comprising:
an executable portion that receives, by a dialog system, data representative of a user profile, a domain knowledge, and historical questions associated with historical questionnaires for each of a plurality of users;
an executable portion that trains, using one or more deep learning operations executed by machine learning logic, the dialog system to automatically and adaptively generate one or more customized questions or questionnaires using the data, wherein the training includes initially grouping each of the plurality of users into clusters according to characteristics identified in the data;
an executable portion that, subsequent to initially grouping each of the plurality of users into the clusters, generating the one or more customized questions or questionnaires according to an analysis of the data, and to which of the clusters each of the plurality of users currently belongs, by the one or more deep learning operations in conjunction with one or more current responses to one or more current queries iteratively provided to a selected user by the dialog system subsequent to initially generating the one or more customized questions or questionnaires, wherein, the one or more customized questions or questionnaires are initially generated using only textual content of the data, and any spoken interaction comprising spoken utterances between the dialog system and the user subsequent to the initial generation and with respect to the one or more current queries is to resolve uncertainties in the data when generating further questions of the one or more customized questions or questionnaires for the user; and
an executable portion that, responsive to the one or more current responses from the selected user yielding an inconclusive result that currently updates a placement of the selected user into conflicting clusters, dynamically updating the one or more customized questions or questionnaires in real time by automatically generating intermediate questions during the one or more current queries to resolve the inconclusive result and determine which of the clusters the selected user currently belongs prior to continuing with the one or more customized questions or questionnaires.

14. The computer program product of claim 13, further including an executable portion that:
determines a selected order for delivering the one or more customized questions or questionnaires using a dialog system; and
dynamically adjusts the selected order of the one or more customized questions or questionnaires according to a response provided to a previous query.

15. The computer program product of claim 13, further including an executable portion that collects feedback information relating to the one or more customized questions or questionnaires.

16. The computer program product of claim 13, further including an executable portion that determines a degree of relevance of the one or more customized questions or questionnaires according to contextual information and collected feedback data.

17. The computer program product of claim 13, further including an executable portion that initializes a machine learning mechanism to apply one or more machine learning models or rules to generate the one or more customized questions or questionnaires for the selected user, taking into account previously collected feedback, modify the one or more customized questions or questionnaires, learning customized questions pertaining to the similar profiles of the alternative users, analyze the one or more current responses to the one or more current queries, or perform a combination thereof.

\* \* \* \* \*